US00PP14684P29

(12) United States Plant Patent
Trees

(10) Patent No.: US PP14,684 P2
(45) Date of Patent: Apr. 6, 2004

(54) LANTANA PLANT NAMED 'BALUCYELL'

(50) Latin Name: *Lantana camara*
Varietal Denomination: Balucyell

(75) Inventor: Scott C. Trees, Shell Beach, CA (US)

(73) Assignee: Ball FloraPlant, a division of Ball Horticultural Co., West Chicago, IL (US)

( * ) Notice: Subject to any disclaimer, the term of this patent is extended or adjusted under 35 U.S.C. 154(b) by 31 days.

(21) Appl. No.: 10/329,860

(22) Filed: Dec. 26, 2002

(51) Int. Cl.[7] ..... A01H 5/00
(52) U.S. Cl. ..... Plt./227
(58) Field of Search ..... Plt./227

*Primary Examiner*—Kent Bell
(74) *Attorney, Agent, or Firm*—Wood, Phillips, Katz, Clark & Mortimer

(57) ABSTRACT

A new and distinct Lantana plant named 'Balucyell', characterized by its yellow flowers, upright growth habit, and dark green foliage.

2 Drawing Sheets

Latin name of genus and species of plant claimed: *Lantana camara.*
Variety denomination: 'Balucyell'.

BACKGROUND OF INVENTION

The present invention comprises a new and distinct Lantana plant, botanically known as *Lantana camara*, and hereinafter referred to by the cultivar name 'Balucyell'.

The new cultivar was developed by the inventor in a controlled breeding program during 1999, at Arroyo Grande, Calif. The objective of the breeding program was the development of Lantana cultivars with a well-branched, compact habit, continuous flowering and dark green foliage.

The female (seed) parent of 'Balucyell' was the commercially available Lantana variety 'Simon Red' (not patented), characterized by its red flowers and upright growth habit. The male (pollen) parent of 'Balucyell' was the commercially available Lantana variety 'Pink Caprice' (not patented), which exhibits an upright habit and pink/yellow flowers. 'Balucyell' was selected in May 2000 as a single flowering plant from within the progeny of the above stated cross and was initially designated '42-3'.

Asexual reproduction of the new cultivar at Arroyo Grande, Calif. and West Chicago, Ill. was carried out by the use of terminal stem cuttings has demonstrated that the new Lantana reproduces true to type with the characteristics as herein described are firmly fixed and retained through successive generations of such asexual propagation.

SUMMARY OF INVENTION

It was found that the cultivar of the present invention:

(a) exhibits yellow flowers, (b) forms dark green foliage, and (c) exhibits an upright mounded growth habit.

The new cultivar of the present invention can be compared to the commercially available Lantana variety, Patriot 'Sunbeam' (not patented) and to its male parent, 'Pink Caprice'. In side-by-side comparison, plants of the new cultivar differ from plants of 'Sunbeam'. It is found that the new cultivar is taller and narrower, has larger leaves and more flowers per inflorescence than 'Sunbeam'. When compared to 'Pink Caprice', it is found that the new cultivar has a more compact habit, slightly larger leaves and flowers of a lighter yellow color.

BRIEF DESCRIPTION OF PHOTOGRAPH

The accompanying photographs show as nearly true as it is reasonably possible to make the same in color illustrations of this type, typical flower and foliage characteristics of the new cultivar. The plants were grown for 7 weeks in a greenhouse at West Chicago, Ill.

DETAILED BOTANICAL DESCRIPTION

Figure 1:
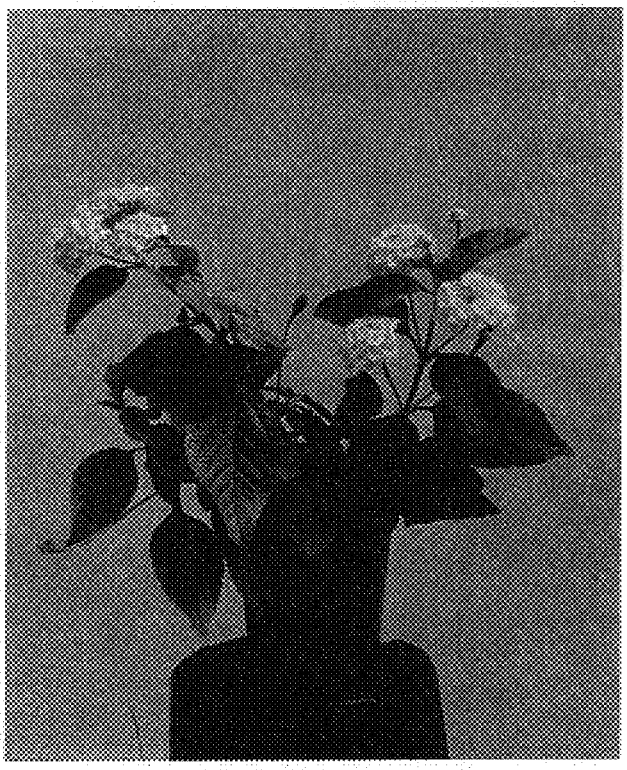
FIG. 1 illustrates the overall growth habit of the new cultivar.
Figure 2:
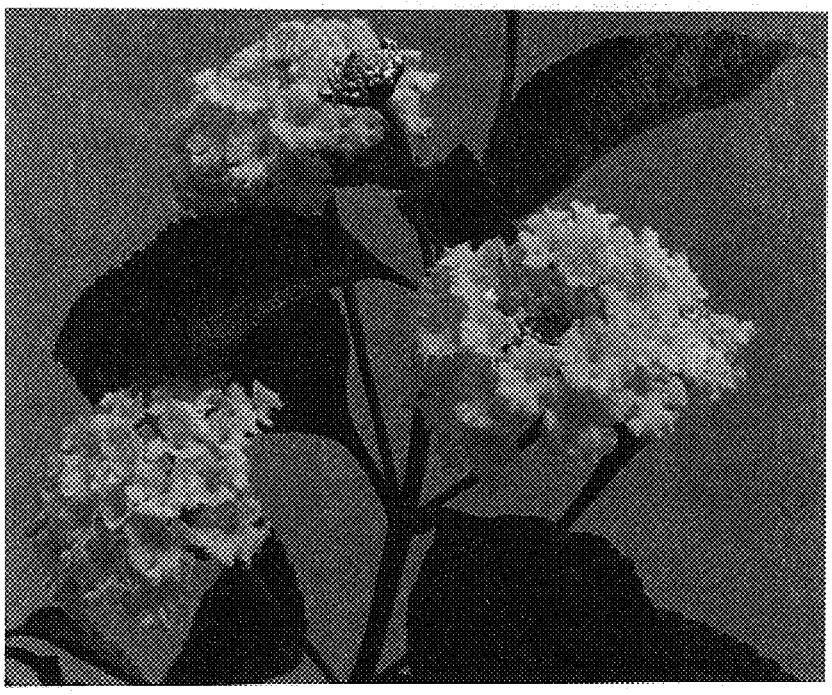
FIG. 2 illustrates a close up view of a bud, leaves and three inflorescence of the new cultivar.

The new cultivar has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Apr. 15, 2002. The readings were taken between 1:00 and 3:00 p.m. under natural daylight conditions. The plants were produced from cuttings taken from stock plants and were grown in a double polycarbonate covered greenhouse under conditions comparable to those used in commercial practice. The plants were grown for 7 weeks while utilizing a soilless growth medium and maintaining temperatures of approximately 75° to 85° F. (24° to 29° C.) during the day and approximately 62° to 68° F. (17° to 20° C.) during the night and light levels of 4,000 to 10,000 footcandles.

Classification:
*Botanical.*—*Lantana camara* cultivar 'Balucyell'.
Parentage:
*Female parent.*—'Simon Red'.
*Male parent.*—'Pink Caprice'.
Propagation:
*Type cutting.*—Terminal tip.
*Time to initiate roots.*—Approximately 14 to 21 days.
*Root description.*—Fibrous, branching.

Plant description:

*Habit of growth.*—Moderately vigorous. Pinching improves branching. A mature plant, 7 weeks after the planting of a rooted cutting, measures approximately 25.1 cm in height and approximately 14.6 cm in width with 1.3 main branches.

*Form.*—Upright, mounded.

*Branch.*—Square, approximately 22.6 cm in length and 3 mm in diameter, with moderate amount of long stiff hairs. Color is 146B. Internode length at middle of stem is approximately 3.8 cm.

*Foliage.*—Leaves are opposite, ovate with serrate/crenate margin, acute apex and attenuate base. Upper surface is densely covered with short, stiff hairs. Lower surface is moderately covered with short stiff hairs. Leaf length is approximately 9.3 cm and width is approximately 5.1 cm. Upper surface of mature foliage is 137A and lower surface is lighter and greyer than 137C. Upper and lower surfaces have pinnate-reticulate venation. Color of venation on upper surface is 145A. Color of venation on lower surface is 145C. Petiole surface is moderately covered with stiff hairs of moderate length, length is approximately 1.1 cm, diameter is approximately 2 mm and color is 145C.

Flowering description:

*Flowering habit.*—Freely flowering.

*Natural flowering season.*—Year round in greenhouse environment and spring through autumn in outdoor garden.

Inflorescence description. Type: Terminal heads. Shape: Spherical. Approximately 2.4 cm in depth and approximately 4.7 cm in diameter with approximately 32 fully open flowers at any one time. Each flower is subtended by a single bract. Flowers are sessile.

*Bract.*—Shape: Lanceolate. Length: Approximately 6 mm. Width: Approximately 1 mm. Apex: Acute. Margin: Entire. Both surfaces are slightly pubescent. Upper and lower surface color: 144B.

*Peduncle.*—Shape: Rectangular. Length: Approximately 8.1 cm. Diameter: Approximately 1 mm. Aspect: at acute angle to branch, Texture: Moderately covered with short stiff hairs. Color: 144B with short stiff hairs.

Flower description:

*Fragrance.*—Light, herbal.

*Aspect.*—Concave.

*Lastingness of bloom.*—Approximately 6–9 days.

*Bud.*—Square, pillow shaped, approximately 4 mm in width and 3 mm in depth and 13A in color.

*Petals.*—Five, non-overlapping. Fused at base to form corolla tube. Upper petal: Shape: Obovate. Apex: Broadly acute. Margin: Entire, undulate. Length from throat: Approximately 7 mm. Width: Approximately 8 mm. Lateral petals: Shape: Obovate. Apex: Obtuse. Margin: Entire, undulate. Length from throat: Approximately 5 mm. Width: Approximately 8 mm. Lower petal: Shape: Obovate. Apex: Obtuse. Margin: Entire, undulate. Length from throat: Approximately 6 mm. Width: Approximately 6 mm. Texture of all petals: Smooth and glabrous.

*Corolla.*—Diameter is approximately 1.4 cm. Petal color when first open: 9A. Petal color when fully open: Upper surface is 14B at margin, 14A in center. Color of lower surface is 14C. Upper and lower surfaces of petals are smooth.

*Corolla tube.*—Length is approximately 1.5 cm, diameter at tube opening is approximately 1 mm, diameter at base is approximately 1 mm. Pubescence of outer surface is dense. Color of outer surface: 14C. Inner surface of tube is smooth except for hairs around opening. Color of inner surface is 14D.

*Calyx.*—Tubular, formed by 5 fused sepals with acute tips. Length: Approximately 3 mm. Diameter: Approximately 1 mm. Color of both surfaces: 145C.

*Reproductive organs.*—There are 4 stamens fused to the corolla tube. The anther length is 1 mm and the color is 165B. Pollen is sparse and 18D in color. There is one pistil, 4 mm in length. The stigma shape is round, the length is less than 1 mm and the color is 150B. The style length is approximately 2 mm and the color is 150D. Ovary length is 1 mm and color is 150B.

Seed/fruit production: Seed/fruit production has not been observed.

Disease resistance: Resistance to pathogens has not been observed.

Hardiness zone: 'Balucyell' is hardy in zones nine (9) and above.

I claim:

1. A new and distinct *Lantana camara* plant named 'Balucyell' substantially as herein shown and described, which:

(a) exhibits yellow flowers, (b) forms dark green foliage, and (c) exhibits an upright growth habit.

* * * * *